(12) United States Patent
Suzuki

(10) Patent No.: US 11,369,308 B2
(45) Date of Patent: Jun. 28, 2022

(54) SWALLOWING ACTION MEASUREMENT DEVICE AND SWALLOWING ACTION SUPPORT SYSTEM

(71) Applicant: PLIMES Inc., Ibaraki (JP)

(72) Inventor: Kenji Suzuki, Tsukuba (JP)

(73) Assignee: PLIMES INC., Ibaraki (JP)

( * ) Notice: Subject to any disclaimer, the term of this patent is extended or adjusted under 35 U.S.C. 154(b) by 320 days.

(21) Appl. No.: 16/276,768

(22) Filed: Feb. 15, 2019

(65) Prior Publication Data

US 2019/0175093 A1 Jun. 13, 2019

Related U.S. Application Data

(63) Continuation of application No. PCT/JP2017/029149, filed on Aug. 10, 2017.

(30) Foreign Application Priority Data

Aug. 15, 2016 (JP) .............................. JP2016-159263

(51) Int. Cl.
*A61B 5/00* (2006.01)
*A61B 5/11* (2006.01)
(Continued)

(52) U.S. Cl.
CPC ............ *A61B 5/4205* (2013.01); *A61B 5/107* (2013.01); *A61B 5/11* (2013.01); *A61B 5/6822* (2013.01);
(Continued)

(58) Field of Classification Search
CPC ......... A61B 5/42; A61B 5/4205; A61B 5/107; A61B 5/11; A61B 5/6822; A61B 5/08;
(Continued)

(56) References Cited

U.S. PATENT DOCUMENTS

2009/0030346 A1 1/2009 Kojima et al.
2009/0227907 A1 9/2009 Kandori et al.
(Continued)

FOREIGN PATENT DOCUMENTS

CN 103458777 A * 12/2013 ........... A61B 5/1126
CN 104898829 A * 9/2015 ............... A61B 5/11
(Continued)

OTHER PUBLICATIONS

Extended European Search Report for EP Application No. 17841462. 9, dated Apr. 2, 2020.
(Continued)

*Primary Examiner* — Patrick Fernandes
*Assistant Examiner* — Severo Antonio P Lopez
(74) *Attorney, Agent, or Firm* — Burris Law, PLLC

(57) ABSTRACT

A swallowing action measurement device includes a holder, a sound detector and a posture detector. The holder is fitted to a neck region of a person being measured from behind. The sound detector is held in the holder in contact with the outer side surface of the neck region close to the epiglottis, and detects sound associated with at least a swallowing action of the person being measured and outputs a measured sound signal. The posture detector detects a posture of the person being measured.

23 Claims, 9 Drawing Sheets

(51) Int. Cl.
*A61B 5/107* (2006.01)
*A61B 5/08* (2006.01)
*A61B 7/00* (2006.01)

(52) U.S. Cl.
CPC . *A61B 5/08* (2013.01); *A61B 5/45* (2013.01); *A61B 5/6831* (2013.01); *A61B 7/008* (2013.01)

(58) Field of Classification Search
CPC ....... A61B 5/45; A61B 5/6801; A61B 5/6831; A61B 7/008; A61B 7/04; A61B 5/112; A61B 5/1123; A61B 5/1124; A61B 5/1126; A61B 5/1127; A61B 5/1128; A61B 5/0059; A61B 5/6887; A61B 5/6888; A61B 5/6898; G01K 9/00348
See application file for complete search history.

(56) References Cited

U.S. PATENT DOCUMENTS

| | | | | |
|---|---|---|---|---|
| 2009/0292178 | A1* | 11/2009 | Ellis | G16H 40/67 600/301 |
| 2011/0160615 | A1 | 6/2011 | Matsumura | |
| 2011/0276312 | A1* | 11/2011 | Shalon | A61B 5/6838 702/187 |
| 2013/0289434 | A1* | 10/2013 | Chou | A61B 5/394 600/546 |
| 2014/0123912 | A1* | 5/2014 | Menkes | A61B 5/02055 119/859 |

FOREIGN PATENT DOCUMENTS

| | | | | |
|---|---|---|---|---|
| EP | 1787582 | | 5/2007 | |
| JP | 2005304890 | | 11/2005 | |
| JP | 2006095264 | | 4/2006 | |
| JP | 2006263299 | | 10/2006 | |
| JP | 2007202939 | | 8/2007 | |
| JP | 2007202939 A | * | 8/2007 | .......... A61B 5/6822 |
| JP | 2009060936 | | 3/2009 | |
| JP | 2009213592 | | 9/2009 | |
| JP | 2012200300 | | 10/2012 | |
| JP | 2013017694 | | 1/2013 | |
| JP | 2013017694 A | * | 1/2013 | .............. A61B 7/00 |
| JP | 2016045816 | | 4/2016 | |
| JP | 2016045816 A | * | 4/2016 | |

OTHER PUBLICATIONS

International Search Report for International Application PCT/JP2017/029149, dated Oct. 31, 2017.

* cited by examiner

SWALLOWING ACTION MEASUREMENT DEVICE AND SWALLOWING ACTION SUPPORT SYSTEM

CROSS-REFERENCE TO RELATED APPLICATIONS

This application is a continuation of International Application No. PCT/JP2017/029149, filed on Aug. 10, 2017, which claims priority to and the benefit of JP 2016-159263 filed on Aug. 15, 2016. The disclosures of the above applications are incorporated herein by reference.

FIELD

The present disclosure relates to a swallowing action measurement device to detect sound generated from a user's neck region by swallowing action and a swallowing action support system using the swallowing action measurement device.

BACKGROUND

The statements in this section merely provide background information related to the present disclosure and may not constitute prior art.

In general, people's ability to swallow, i.e., their swallowing function declines with advancing age. Elderly people whose swallowing function has declined may have difficulty eating their daily meal. In addition, persons with hemiplegia, a stroke, etc., may develop dysphagia, and the number of patients with dysphagia is increasing every year. The patients with dysphagia are more likely to have aspiration. The aspiration not only increases the risk of suffocation, but also causes aspiration pneumonia by various germs that enter the lungs through the oral cavity.

Pneumonia is one of the main leading cause of death in Japan, and pneumonia is extremely common. The recurrence of pneumonia due to dysphagia is high. If the pneumonia becomes worse, most of the patients thereof will die. The swallowing action is made not only during eating but also unconsciously during sleeping. It is thus necessary to measure the swallowing action continuously including during sleeping, know the degree of a disability of the swallowing function at an early stage and, perform treatment and rehabilitation suitable for the degree of the disability.

Patent literature 1 (JP 2013-017694 A) discloses a swallowing function data measurement device that is attached to the neck region of a user of a measurement target to assess the degree of disability of the swallowing function. This device includes a sound measurement unit built in a frame attached to the neck region to determine whether a food bolus has passed into the esophagus by discriminating among an epiglottis closing sound, a food bolus moving sound and an epiglottis opening sound as pharynx action sounds and light an LED provided toward the outside of the frame in light emission color corresponding to the determination.

Patent literature 2 (JP 2009-060936 A) discloses detecting a vibration due to swallowing sound by an acceleration sensor stuck by tape on the skin surface of a user of a measurement target, which corresponds to a neck region of the user and discriminating among three sounds of an epiglottis closing sound, a food bolus moving sound and an epiglottis opening sound and then displaying a diagnosis result on a monitor. Patent literature 3 (JP 2006-263299 A) discloses a biological signal analysis device including a biological sensor with a microphone built therein, which is attached to the surface of the neck of a user of a measurement target, to acquire a cough, throat clearing, swallowing sound, generated sound and other sound information.

SUMMARY

Even if the degree of disability of a swallowing action is assessed, it is difficult to prevent an erroneous swallowing action so as not to cause aspiration in daily life. When a user of a person being measured undergoes rehabilitation to make a proper swallowing action, a doctor who diagnoses whether there is dysphagia and a caregiver who assists the rehabilitation of dysphagia need to be able to assess the swallowing condition of the user easily and in real time.

If doctors and caregivers use the devices disclosed in patent literatures 1 to 3, they may be able to determine whether a swallowing action is made properly. However, it is difficult for the doctors and caregivers to attend a user when the user wears a device and undergoes rehabilitation for each meal. It is thus important to determine a swallowing action immediately every time and cause a user who has made a swallowing action, a care assistant and the others to know that the swallowing action can be made properly.

There are variations in sound caused from a swallowing action among individuals. Thus, when a device is attached for rehabilitation, it is difficult to set the device for each user such that a swallowing action can be determined properly after the presence or absence of dysphagia is determined based on doctor's diagnosis. To improve the swallowing action properly by rehabilitation, a device for measuring the swallowing action continues to be used at least for a fixed period of time and thereafter in certain cases. In user's daily life, not only it takes time and is complicated to attach and detach the device, but also the device hinders a user from eating a meal whenever his or her swallowing action is determined during the meal.

Accordingly, the present invention provides a swallowing action measurement device which is easy to attach and detach for a user and is capable of measuring a swallowing action without hindering the user from eating his or her meal smoothly and a swallowing action support system using the swallowing action measurement device for rehabilitation of the swallowing action.

A swallowing action measurement device of one embodiment of the present invention comprises a holder, a sound detector and a posture detector. The holder is fitted to a neck region of a person being measured from behind. The sound detector is mounted in the holder in contact with the outer side surface of the neck region close to the epiglottis, and detects sound associated with at least a swallowing action of the person being measured and outputs a measured sound signal. The posture detector detects the neck posture of the person being measured.

The posture detector is attached to the holder located on a median plane of the person being measured, and includes an electronic compass to detect magnetic intensity of earth's magnetism for orthogonal three axes and outputs a measured posture signal including the magnetic intensity.

At this time, it is preferable that the posture detector detects acceleration in a direction along the orthogonal three axes and angular velocity with each of the orthogonal three axes as a center axis and outputs the acceleration and the angular velocity with the acceleration and the angular velocity included in the measured posture signal. The sound detector may also include a pair of vibration detectors disposed plane-symmetrically with regard to the median plane. Furthermore, the sound detector may include a pair of vibration detectors disposed along a direction in which a food bolus is moved by the swallowing action. It is also preferable that the posture detector includes a plurality of posture detectors disposed along a direction in which a food bolus is moved by the swallowing action and each of the posture detectors outputs the measured posture signal.

The foregoing swallowing action measurement device further comprises an analysis unit, a determination unit, a controller and a memory. The analysis unit discriminates among epiglottis closing sound, food bolus moving sound and epiglottis opening sound from the measured sound signal based upon frequency characteristics and outputs the epiglottis closing sound, food bolus moving sound and epiglottis opening sound as a series of items of swallowing action information in association with the measured posture signal in real time when each sound is detected. The determination unit compares predetermined temporal characteristics and frequency characteristics of the measured sound signal included in the swallowing action information in real time with predetermined temporal characteristics and frequency characteristics of a standard sound signal preset for the swallowing action, and outputs a proper signal indicating that the swallowing action is in a proper state while a deviation is within a predetermined range and outputs an improper signal indicating that the swallowing action is in an improper state when the deviation exceeds the predetermined range. The controller outputs the swallowing action information as swallowing information unique to the person being measured in association with the proper signal and the improper signal. The memory stores the standard sound signal and the unique swallowing information.

When the sound detector includes a pair of vibration detectors disposed plane-symmetrically with regard to the median plane, the analysis unit determines whether the swallowing action is dominant on the right or dominant on the left, based on a difference between right and left measured sound signals detected by the pair of vibration detectors, and outputs a determination result in addition to the swallowing action information. Alternatively, when the sound detector includes a pair of vibration detectors disposed plane-symmetrically with regard to the median plane, the analysis unit determines whether the swallowing action is dominant on the right or dominant on the left, based on a difference between right and left measured sound signals detected by the pair of vibration detectors and the measured posture signal, and outputs a determination result in addition to the swallowing action information.

Furthermore, when the sound detector includes a pair of vibration detectors disposed along a direction in which a food bolus is moved by the swallowing action, the analysis unit calculates a speed of motion of the food bolus based on the measured sound signal detected by the pair of vibration detectors and outputs the speed of motion in addition to the swallowing action information. When the posture detector includes a plurality of posture detectors disposed along a direction in which a food bolus is moved by the swallowing action and each of the posture detectors outputs the measured posture signal, the analysis unit calculates a turn, a bending direction and a bending angle of the neck region based on the measured signal output from each of the plurality of posture detectors and outputs the turn, bending direction and bending angle in addition to the swallowing action information.

The foregoing swallowing action measurement further comprises a control unit, a first communication unit and a second communication unit. The control unit is located away from the holder and within a range where the control unit is allowed to be operated by the person being measured and is equipped with the analysis unit, the determination unit, the controller and the memory. The first communication unit is built in the holder to transmit a signal including at least the measured sound signal and the measured posture signal. The second communication unit is built in the control unit to receive a signal including at least the measured sound signal and the measured posture signal. The "signal including at least the measured sound signal and the measured posture signal" may include the swallowing action information output from the analysis unit, the proper signal and improper signal output from the determination unit, and the unique swallowing information output from the controller.

At this time, the first communication unit and the second communication unit may wirelessly communicate with each other. Also, the analysis unit, the determination unit, the controller and the memory may be incorporated into the holder. Furthermore, the swallowing action measurement device may further comprise a battery mounted on the holder and configured to supply power to the sound detector, the posture detector, the analysis unit, the determination unit, the controller and the memory.

To calibrate the swallowing action measurement device according to the person being measured, the controller averages the measured sound signals included in the unique swallowing information associated with the proper signal, among past unique swallowing information stored in the memory, and replaces the standard sound signal stored in the memory with the averaged signal. Alternatively, the swallowing action measurement device further comprises input means for starting and terminating measurement for calibration of the sound detector and the posture detector, and the controller stores the measured sound signal and the measured posture signal, which are detected from start to end of the calibration, in the memory as the standard sound signal and the standard posture signal, respectively. Alternatively, the controller averages the measured posture signals included in the unique swallowing information associated with the proper signal, among past unique swallowing information stored in the memory, and stores an averaged signal in the memory as the standard posture signal. Then, the determination unit compares the measured posture signal with the standard posture signal, and outputs the proper signal while a deviation is within a predetermined range and outputs the improper signal when the deviation exceeds the predetermined range.

A swallowing action support system of one embodiment of the present invention comprises a holder, a sound detector, a posture detector, an analysis unit, a determination unit, a controller, a notification unit and a memory. The holder is fitted to a neck region of a person being measured from behind. The sound detector is held in the holder in contact with the outer side surface of the neck region close to the epiglottis to detect sound associated with at least a swallowing action of the person being measured and output a measured sound signal. The posture detector is attached to the holder located on a median plane of the person being measured, and includes an electronic compass to detect magnetic intensity of earth's magnetism for orthogonal three axes and outputs a measured posture signal including the magnetic intensity. The analysis unit discriminates among epiglottis closing sound, food bolus moving sound and epiglottis opening sound from the measured sound signal based upon frequency characteristics and outputs the epiglottis closing sound, food bolus moving sound and epiglottis opening sound as a series of items of swallowing action information in association with the measured posture signal in real time when each sound is detected. The determination unit compares predetermined temporal characteristics and frequency characteristics of the measured sound signal included in the swallowing action information in real time with predetermined temporal characteristics and frequency characteristics of a standard sound signal preset for the swallowing action, and outputs a proper signal indicating that the swallowing action is in a proper state while a deviation is within a predetermined range and outputs an improper signal indicating that the swallowing action is in an improper state when the deviation exceeds the predetermined range. The controller outputs the swallowing action information as swallowing information unique to the person being measured in association with the proper signal and the improper signal and outputs a first command signal corresponding to the proper signal and a second command signal corresponding to the improper signal. The notification unit makes a first notification in response to the first command signal and makes a second notification different from the first notification, in response to the second command signal. The memory stores the standard sound signal and the unique swallowing information.

At this time, the posture detector detects acceleration in a direction along the orthogonal three axes and angular velocity with each of the orthogonal three axes as a center axis and outputs the acceleration and the angular velocity with the acceleration and the angular velocity included in the measured posture signal.

The swallowing action support system further comprises an external unit, a first communication device and a second communication device. The external unit is located away from the holder and within a range where the external unit is allowed to be perceived by the person being measured. The first communication device transmits the first command signal and the second command signal wirelessly. The second communication device is built in the external unit to receive the first command signal and the second command signal wirelessly. The notification unit includes an external light source disposed in at least the external unit to cause the external light source to emit light in a first light emission pattern as the first notification when the notification unit detects the first command signal and cause the external light source to emit light in a second light emission pattern other than the first light emission pattern, as the second notification when the notification unit detects the second command signal.

The swallowing action support system may further comprise a control unit. The control unit is located away from the holder and within a range where the control unit is allowed to be operated by the person being measured and is equipped with the analysis unit, the determination unit, the controller, the memory and the first communication device. Alternatively, in the swallowing action support system, the holder may be equipped with the analysis unit, the determination unit, the controller, the memory and the first communication device.

The notification unit includes a pair of holder light sources disposed in the holder plane-symmetrically with regard to the median plane to cause the holder light sources to emit light in a first light emission pattern as the first notification when the notification unit detects the first command signal and cause the holder light sources to emit light in a second light emission pattern other than the first light emission pattern, as the second notification when the notification unit detects the second command signal.

When the first communication device is connectable to a communication network to which a database and a management terminal are connected, the controller may store the unique swallowing information in the database together with identification information of the person being measured. Also, in a case where the swallowing action support system further comprises input means operated for calibration of the sound detector and the posture detector, when the input means is operated, the controller averages the measured sound signals and the measured posture signals included in the unique swallowing information associated with the proper signal, selected from among the unique swallowing information stored in the database, based on the identification information and stores averaged signals in the memory as the standard sound signal and the standard posture signal, respectively.

According to the swallowing action measurement device of one embodiment of the present invention, a holder fitted to the neck region of a person being measured is equipped with a posture detector. It is thus possible to easily determine whether the swallowing action measurement device can be attached properly each time the device is attached to measure sound associated with a swallowing action. Thus, the swallowing action measurement device is easy to attach and detach for users including doctors and caregivers as well as the person being measured, and the device is capable of measuring a swallowing action without hindering a user from eating his or her meal smoothly.

According to the swallowing action support system of one embodiment of the present invention, the use of the foregoing swallowing action measurement device makes it possible to know whether each swallowing action is proper in real time by notification means, while the device is easy to attach and detach. Therefore, the swallowing action support system can easily be introduced into rehabilitation of a swallowing action.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

Accordingly, further areas of applicability will become apparent from the description provided herein. It should be understood that the description and specific examples are intended for purposes of illustration only and are not intended to limit the scope of the present disclosure.

DRAWINGS

The accompanying drawings, which are incorporated in and constitute a part of the specification, illustrate embodiments of the invention, and together with the general description given above and the detailed description of the embodiments given below, serve to explain the principles of the invention.

Figure 1:
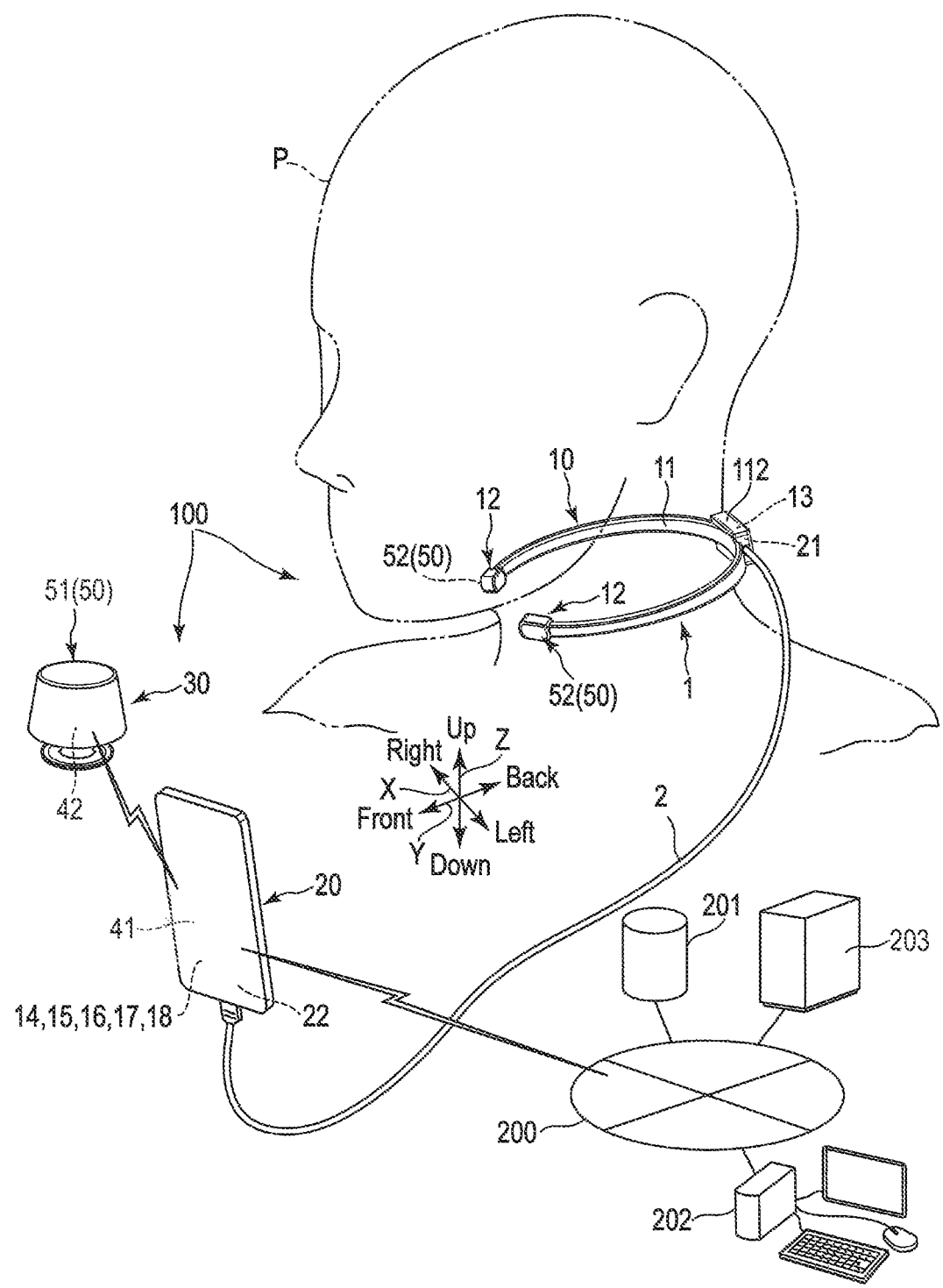
FIG. 1 is a perspective view showing a swallowing action support system including a swallowing action measurement device of a first embodiment of the present invention.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

One of the embodiments of the present invention will be described hereinafter with reference to the accompanying drawings.

A swallowing action support system 100 including a swallowing action measurement device 1 of a first embodiment of the present invention will be described with reference to FIGS. 1 to 6. For convenience of the following descriptions, "front," "back," "right" and "left" will be defined with reference to a person being measured P to which the swallowing action measurement device 1 is attached. Also, the head top side of the person being measured P may be referred to as "up" and the foot side thereof may be referred to as "down."

FIG. 1 shows a measurement unit 10 of the swallowing action measurement device 1, which is attached to the neck region of the person being measured P. The swallowing action measurement device 1 is connected to a smartphone as a control unit 20 via a communication cable 2. The swallowing action measurement device 1 is used to detect and record the sound of the epiglottis movement when the person being measured P is swallowing and determine whether the swallowing action of the person being measured P is performed correctly based on the motion sound of the epiglottis. Since the control unit 20 is a smartphone in the present embodiment, measured data and determination results are displayed on a display section of the control unit 20 and stored in a database 201 connected to a network 200 via a first communication device 41 mounted on the control unit 20.

Furthermore, it is assumed that the swallowing action measurement device 1 is also utilized for part of the swallowing action support system 100 which the person being measured P uses for rehabilitation of his or her swallowing action. In this case, even for rehabilitation, the person being measured P cannot enjoy his or her usual meal because he or she has to check the display section of the control unit 20 during the meal. Therefore, the swallowing action measurement device 1 of the present embodiment includes an external unit 30 to notify the person being measured P of the determination as to whether the swallowing action has been properly performed, as shown in FIG. 1.

Figure 2:
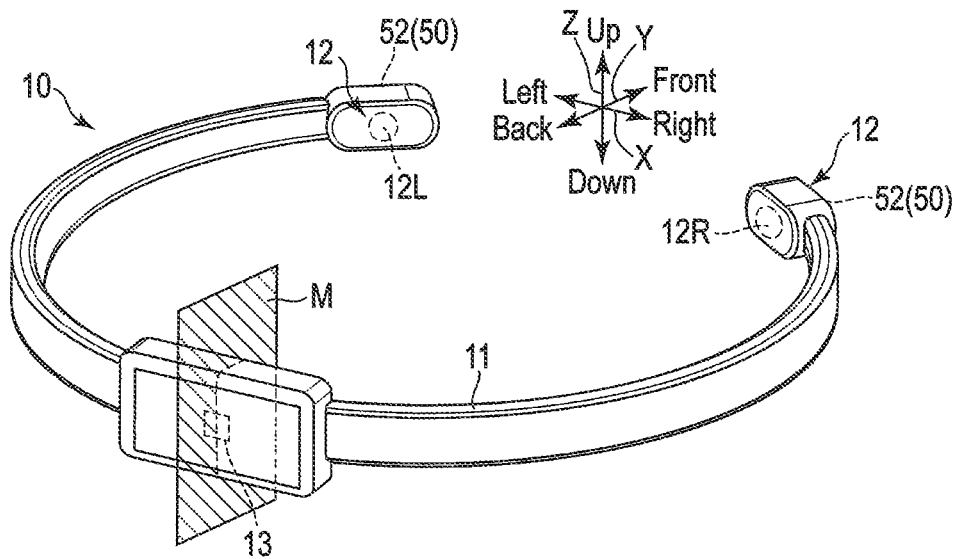
FIG. 2 is a perspective view of the swallowing action measurement device of FIG. 1, viewed from upper right behind.
Figure 3:
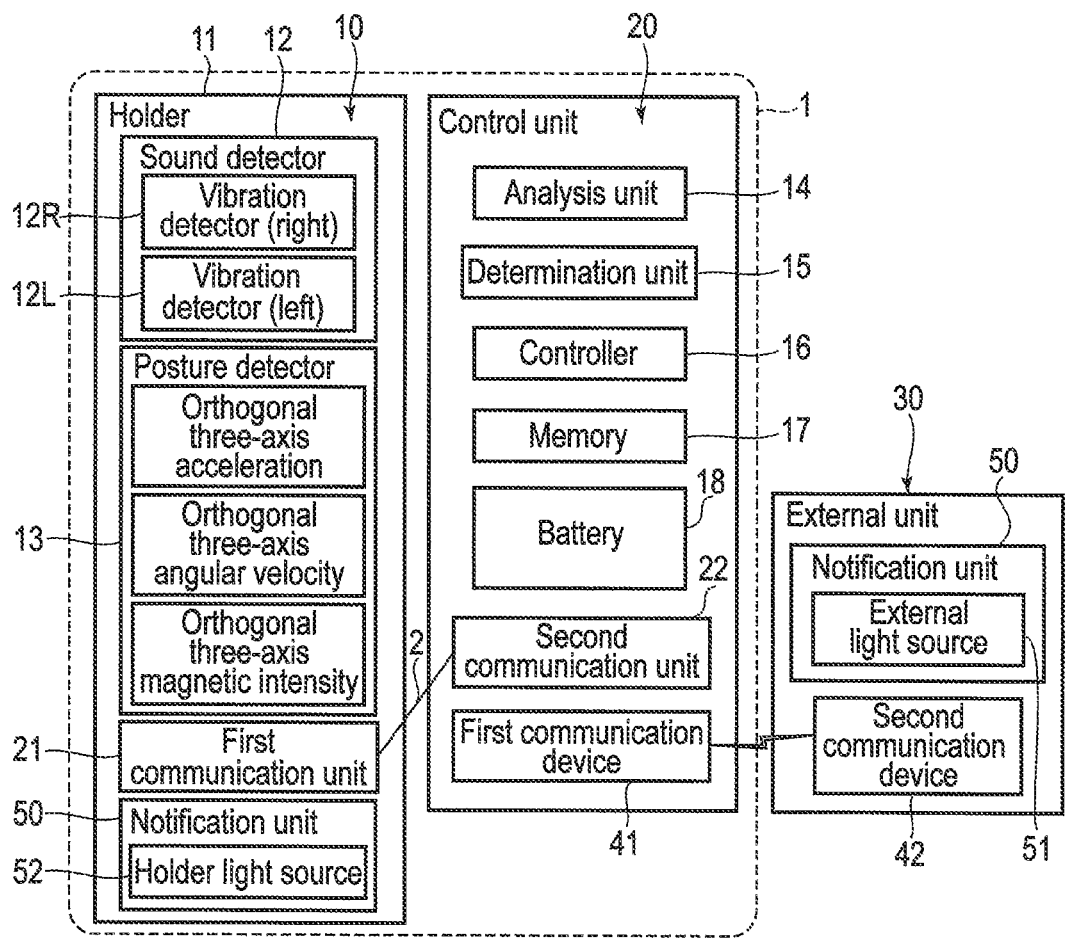
FIG. 3 is a block diagram of the swallowing action measurement device of FIG. 1.

FIG. 2 is a perspective view of the measurement unit 10 of the swallowing action measurement device 1 to be attached to the neck region of the person being measured P, viewed from upper right behind. FIG. 3 is a block diagram showing a configuration of the swallowing action measurement device 1 and the swallowing action support system 100 using the swallowing action measurement device 1. According to FIG. 3, the swallowing action measurement device 1 is configured by the measurement unit 10 and the control unit 20. The swallowing action support system 100 is configured by the external unit 30 in addition to the measurement unit 10 and the control unit 20.

Figure 4:
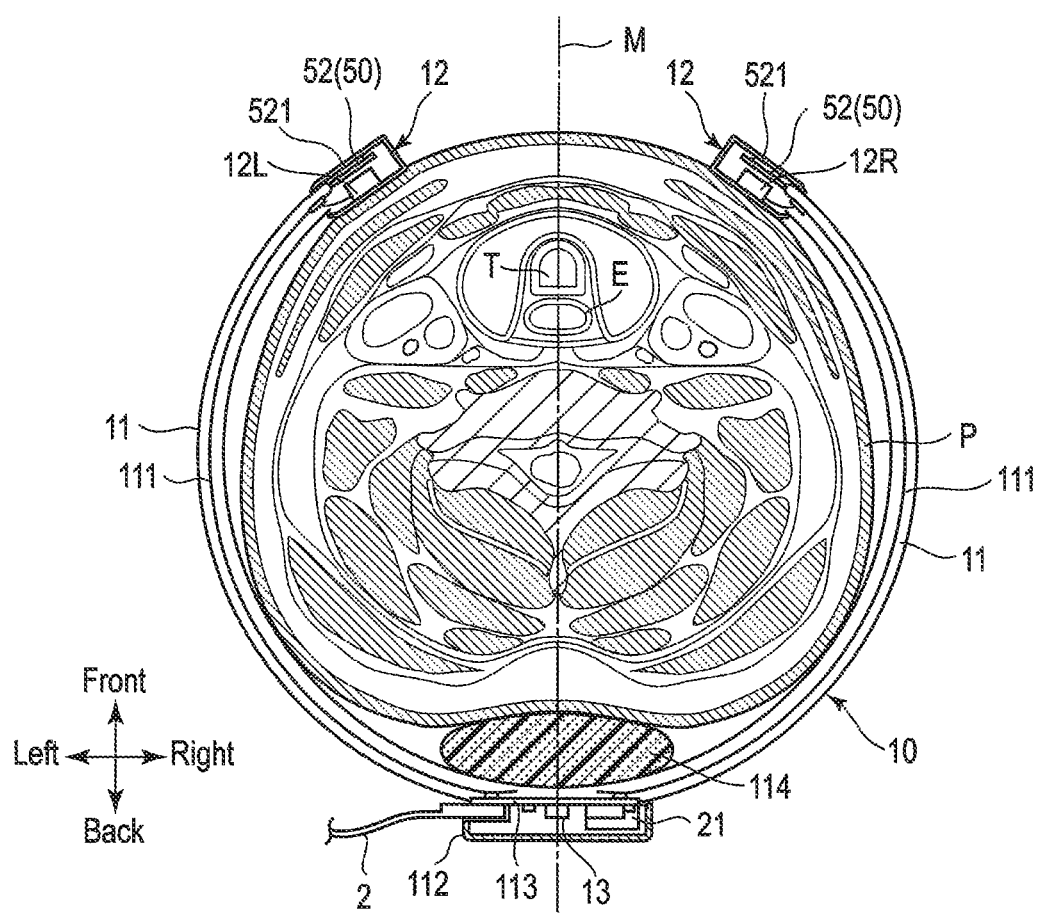
FIG. 4 is a sectional view of the swallowing action measurement device of FIG. 2.
Figure 5:
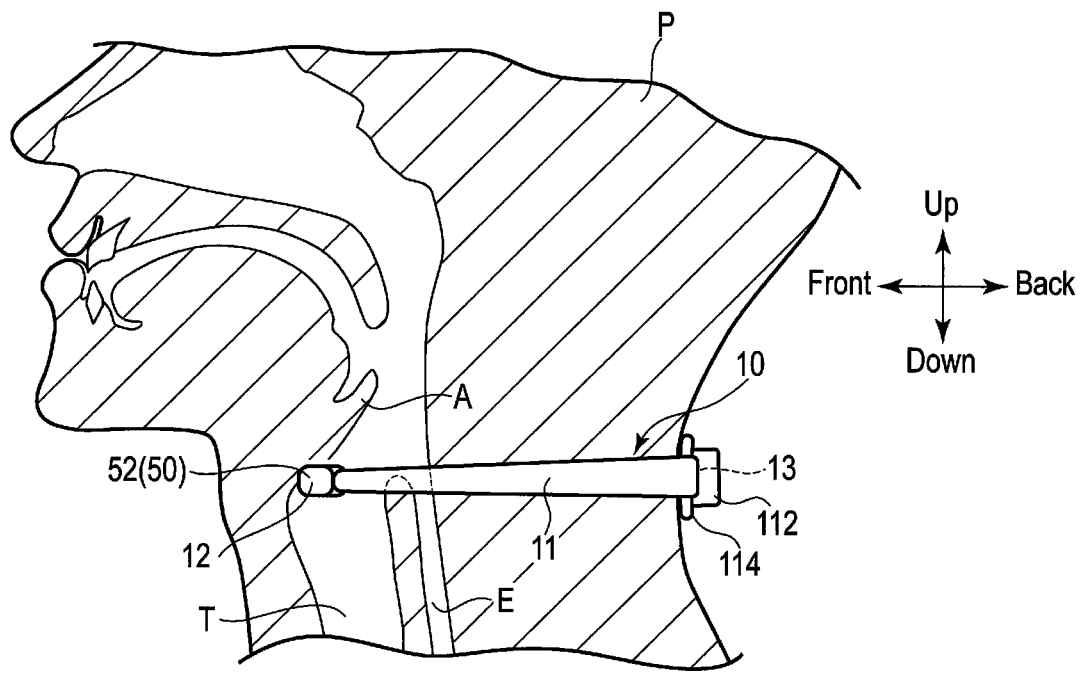
FIG. 5 is a side view of the swallowing action measurement device of FIG. 2, which is attached to a person being measured.

The measurement unit 10 includes a holder 11, a sound detector 12 and a posture detector 13. The holder 11 is fitted from behind the neck region of the person being measured P, as shown in FIGS. 1, 4 and 5. FIG. 4 is a sectional view of the measurement unit 10 for the neck region in a position where the measurement unit 10 is attached. FIG. 5 is a side view of the measurement unit 10, viewed from its left side to correspond to the section along median plane M in order to clarify the position of the measurement unit 10 attached to the neck region of the person being measured P.

The holder 11 is formed of an elastic member with stability, such as hard polyurethane rubber and is flexible to such a degree that it does not constrict the neck region strongly when it is wound on the neck region. Note that a core material made of soft iron or aluminum alloy can be embedded in the holder 11 to maintain the shape of the holder that is deformed in accordance with the preference of the person being measured P. Further, a sponge 114 can be interposed between the back of the neck region and the holder 11 as shown in FIGS. 4 and 5 such that the holder 11 can be held in a fixed position with respect to the neck region even though the person being measured P moves.

The sound detection unit 12 is held in the holder 11 in contact with the outer side surface of the neck region close to the epiglottis A, as shown in FIGS. 4 and 5. The sound detector 12 outputs a measured sound signal detected as sound associated with at least the swallowing action of the person being measured P. As shown in FIGS. 1 to 4, the sound detector 12 includes a pair of vibration detectors 12R and 12L disposed plane-symmetrically with regard to the median plane M. The vibration detectors 12R and 12L are connected to a circuit board 113 in a case 112 disposed behind the neck region by a flexible printed circuit board (FPC) 111 that is embedded in the holder 11 as shown in FIG. 4. Note that since the sound detector 12 includes the vibration detectors 12R and 12L that are in contact with the neck region of the person being measured P, sound generated when the person being measured P moves the epiglottis is detected as a vibration propagated to the body. Therefore, noise derived from air vibration generated in the surrounding environment is hardly detected.

The posture detector 13 is attached to the holder 11 located on the median plane M of the person being measured P, as shown in FIGS. 2 and 4. The posture detector 13 detects the posture of the person being measured P. For example, the posture detector 13 detects a difference in direction angle between the direction toward the esophagus from the vicinity of the epiglottis of the person being measured P (i.e., the motion direction of a bolus of food associated with the swallowing action) and the direction of gravitational acceleration. More specifically, the posture detector 13 includes an electronic compass to detect the absolute direction by detecting the magnetic intensity of the earth's magnetism for orthogonal three axes (X, Y, Z). The posture detector 13 outputs a measured posture signal including the detected magnetic intensity (or absolute direction calculated from the magnetic intensity). The posture detector 13 also detects acceleration in a direction along three axes (X, Y, Z) and angular velocity with each of the orthogonal three axes as the center axis, and outputs the detected acceleration and angular velocity with them included in a measured posture signal. The posture detector 13 is mounted on the circuit board 113 in the case 112 as shown in FIG. 4.

In the present embodiment, the posture detector 13 can employ what is called a 9-axis sensor in which one module incorporates a 3-axis acceleration sensor to detect the acceleration of the orthogonal three axes, a 3-axis gyroscope sensor to detect the angular velocity (rotational speed) of the orthogonal three axes, and a 3-axis electronic compass to detect the magnetic intensity of the orthogonal three axes. Note that the posture detector 13 can be configured by both the 3-axis electronic compass and the 6-axis sensor that is obtained by forming a 6-axis acceleration sensor and a three-axis gyroscope sensor integrally as one component.

The swallowing action measurement device 1 of the present embodiment also includes an analysis unit 14, a determination unit 15, a controller 16 and a memory 17, and these are included in the control unit 20 which is located away from the holder 11 and within a range where the control unit can be operated by the person being measured P, as shown in FIG. 3.

The analysis unit 14 discriminates among epiglottis closing sound, food bolus moving sound and epiglottis opening sound, based upon temporal characteristics and frequency characteristics, from the measured sound signal detected by the sound detector 12. The epiglottis closing sound is action sound generated when the epiglottis A blocks a trachea T to prevent the swallowed food bolus from entering the trachea T. The food bolus moving sound is sound generated when the swallowed food bolus flows into the esophagus E. The epiglottis opening sound is action sound generated when the food bolus passes the entrance of the trachea T and then the trachea T is opened again by the epiglottis A. Then, the analysis unit 14 outputs the epiglottis closing sound, food bolus moving sound and epiglottis opening sound as a series of items of swallowing action information in association with the measured posture signal in real time when each sound is detected.

The determination unit 15 compares predetermined temporal characteristics and frequency characteristics of the measured sound signal included in the swallowing action information in real time with predetermined temporal characteristics and frequency characteristics of a standard sound signal preset for the swallowing action. When the determination unit 15 determines that the swallowing action is in a proper state while the deviation is within a predetermined range, it outputs a proper signal. When the determination unit 15 determines that the swallowing action is in an improper state when the deviation exceeds the predetermined range, it outputs an improper signal. Furthermore, the determination unit 15 may output a proper signal and an improper signal and grades the swallowing action in accordance with the magnitude of the deviation to evaluate the swallowing action as a swallowing function and thus to quantify the degree of dysphagia. Here, the "predetermined temporal characteristics" include, for example, the duration of sound and a parameter that varies with the fluidity of a food bolus.

The controller 16 outputs the swallowing action information, which is output from the analysis unit 14, as swallowing information unique to the person being measured P in association with the proper signal and improper signal output from the determination unit 15. The memory 17 stores the standard sound signal of the swallowing action, which is a basis for comparing it with the measured sound signal, and the unique swallowing information output from the controller 16.

The swallowing action measurement device 1 of the present embodiment includes a pair of right and left vibration detectors 12R and 12L as the sound detector 12 of the measurement unit 10. Thus, the analysis unit 14 determines whether the swallowing action is dominant on the right or dominant on the left, based on the difference between the right and left measured sound signals detected by the paired vibration detectors 12R and 12L, and outputs a result in addition to the swallowing action information. Thus, the unique swallowing information stored in the memory 17 includes a determination result as to whether the right swallowing action is dominant or the left swallowing action is dominant.

In the swallowing action measurement device 1 of the present embodiment, the measurement unit 10 also includes the posture detector 13. It is thus preferable that the analysis unit 14 determines whether the right swallowing action is dominant or the left swallowing action is dominant by the measured posture signal as well as the difference in measured sound signal between the vibration detectors 12R and 12L, and outputs the result in addition to the swallowing action information.

As shown in FIGS. 1 and 3, in the swallowing action measurement device 1 of the first embodiment, the measurement unit 10 and the control unit 20 are provided separately. Specifically, the control unit 20 is placed away from the holder 11 and within a range where the control unit can be operated by the person being measured P. Then, the sound detector 12 and the posture detector 13 are incorporated into the holder 11 of the measurement unit 10. The analysis unit 14, determination unit 15, controller 16 and memory 17 are incorporated into the control unit 20.

Therefore, in order to use the measured sound signal detected by the sound detector 12 and the measured posture signal detected by the posture detector 13 in the analysis unit 14, determination unit 15 and controller 16, first and second communication units 21 and 22 are provided between the measurement unit 10 and the control unit 20. The first communication unit 21 is built in the holder 11 to transmit a signal including at least the measured sound signal and the measured posture signal. The second communication unit 22 is built in the control unit 20 to receive a signal including at least the measured sound signal and the measured posture signal.

In the swallowing action measurement device 1 of the first embodiment, the first communication unit 21 is mounted on the circuit board 113 housed in the case 112 of the holder 11. The second communication unit 22 is incorporated into the smartphone to be used as the control unit 20. The first and second communication units 21 and 22 are connected via the communication cable 2 as shown in FIGS. 1 and 3. Since they are connected via the communication cable 2, a stable communication state is ensured to allow the swallowing action to be determined almost in real time with no time lag.

The control unit 20 includes a battery 18 as shown in FIG. 3 is built. The analysis unit 14, determination unit 15 and controller 16 which are incorporated into the control unit 20 are supplied with power from the battery 18. The sound detector 12 and posture detector 13 incorporated into the holder 11 of the measurement unit 10 are also supplied with power from the battery 18 via the communication cable 2. The supply of power is not limited only to the battery 18, but it is needless to say that power such as commercial power to be supplied to the general household may be supplied via an adapter.

Note that the first and second communication units 21 and 22 may be connected wirelessly to eliminate the inconvenience due to a physical connection using the communication cable 2. In this case, the sound detector 12 and the posture detector 13 of the measurement unit 10 supply power from a battery mounted on the holder 11.

The swallowing action support system 100 further includes a notification unit 50 as shown in FIGS. 1 and 3. The notification unit 50 makes notification that varies between a proper swallowing action and an improper swallowing action in such a manner that the person being measured P easily becomes aware that the swallowing action has been performed properly. In order to operate the notification unit 50, therefore, the controller 16 outputs the unique swallowing information each time the person being measured P performs swallowing action, and outputs a first command signal corresponding to the proper signal output from the determination unit 15 and a second command signal corresponding to the improper signal output from the determination unit 15. The notification unit 50 makes a first notification in response to the first command signal and makes a second notification different from the first notification, in response to the second command signal. That is, the notification unit 50 notifies whether the swallowing action is appropriate each time the person being measured P performs the swallowing action.

The notification unit 50 includes an external light source 51 disposed in at least the external unit 30 to notify at least the person being measured P whether the swallowing action is proper. When the notification unit 50 detects the first command signal, it causes the external light source 51 to emit light in a first light emission pattern as a first notification. When the notification unit 50 detects the second command signal, it causes the external light source 51 to emit light in a second light emission pattern other than the first light emission pattern, as a second notification. Note that the notification unit 50 may make a notification by sound or vibration in addition to light. The sound is not limited to a single note but may be a short melody. Also, light, sound and vibration may be combined.

In the swallowing action support system 100 of the present embodiment, the notification unit 50 includes the external light source 51 disposed in the external unit 30 and holder light sources 52 disposed in the holder 11 of the measurement unit 10 as shown in FIG. 3. Therefore, not only the person being measured P, but also a caregiver who is beside the person being measured P is notified whether the swallowing action of the person being measured P is in a proper state. Note that power required for the holder light sources 52 is supplied from the battery 18 built in the control unit 20 via the communication cable 2.

The external unit 30 is placed away from the holder 11 and within a range where the external unit can be perceived by the person being measured P, as shown in FIGS. 1 and 3. Here, the perceptible range means a position that comes within sight of the person being measured P when the external unit 30 has a function of making a notification with a visual change as the notification unit 50, a position in which the person being measured P can easily touch the external unit 30 when the external unit 30 has a function of making a notification with a change in sense of touch as the notification unit 50, and a position in which the person being measured P can naturally hear the sound generated from the external unit 30 when the external unit 30 has a function of making a notification with an auditory change as the notification unit 50. In the present embodiment, the notification unit 50 provided in the external unit 30 is the external light source 51 and is intended to make a visual notification, and thus the external unit 30 is placed in a position that comes within sight of the person being measured P.

Furthermore, the external unit 30 is provided independently of the swallowing action measurement device 1 as shown in FIGS. 1 and 3. In the swallowing action support system 100, therefore, the first communication device 41 is included in the control unit 20 and a second communication device 42 is included in the external unit 30. The first communication device 41 transmits first and second command signals wirelessly from the controller 16. The second communication device 42 receives the first and second command signals that are transmitted wirelessly.

Figure 6:
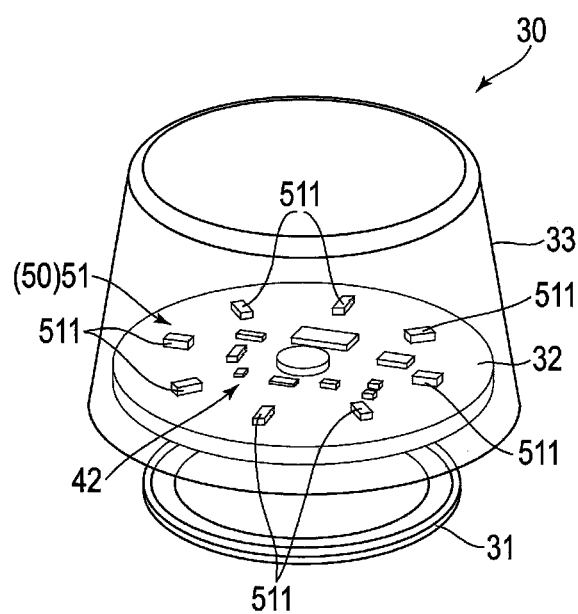
FIG. 6 is a perspective view of an external unit of FIG. 1.

The external unit 30 a self-sustainable leg 31, a circuit board 32 and a lampshade 33 as shown in FIG. 6. On the circuit board 32, a light emitting diode (LED 511) serving as the external light source 51 and the second communication device 42 are mounted. The lampshade 33 covers the external light source 51. The leg 31 of the external unit 30 includes a battery for supplying power to the circuit board 32 or the external unit 30 includes a connector for supplying external power.

The leg 31 may include a sucker, a magnet, a clip, a hook and loop fastener or the like to be firmly fixed. A plurality of LEDs 511 serving as the external light source 51 are mounted on the circuit board 32. Each of the LEDs 511 may be a single-color light emitting diode that emits light in different colors or a light emitting unit in which red, blue and green light-emitting diodes are implemented on one chip so that an emission color can freely be selected.

The lampshade 33 is preferably made of a milk-white translucent member or a translucent member whose inner and outer surfaces are frosted such that the lampshade 33 on the whole is brightened by the light of the LEDs 511. The lampshade 33 has a truncated cone shape as shown in FIG. 6, but the shape of the lampshade 33 is not limited to the truncated cone shape. The lampshade 33 may be shaped like a dome and a square flat panel.

The section of the holder light sources 52 of the notification unit 50 provided in the holder 11 is shown in FIG. 4. As shown in FIG. 4, the holder light sources 52 are disposed in a pair plane-symmetrically with regard to the median plane M. Further, the holder light sources 52 are arranged back to back with respect to the paired right and left vibration detectors 12R and 12L of the sound detector 12. The holder light sources 52 are LEDs like the external light source 51. When the holder light sources 52 detect the first command signal output from the controller 16 via the communication cable 2, they emit light in a first light emission pattern as a first notification. When the holder light sources 52 detect the second command signal output therefrom, they emit light in a second light emission pattern as a second notification.

The first and second light emission patterns executed by the external light source 51 and the holder light sources 52 of the notification unit 50 include not only the number of times the LEDs 511 and 521 turn on and turn off repeatedly but also variations in luminance and lighting in different emission colors.

For example, the external light source 51 emits light in blue or green as the first light emission pattern when the swallowing action is proper, and it emits light in red as the second light emission pattern when the swallowing action is improper. Further, the luminance may be varied in proportion to the intensity of the measured sound signal associated with the swallowing action or the brightness is gently varied in accordance with the swallowing action. For example, the LEDs 511 and 521 are gradually brightened with epiglottis closing sound as a trigger, continues to emit light during the detection of food bolus moving sound, and is gradually darkened with epiglottis opening sound as a trigger. The swallowing action measurement device 1 may include a light sensor to adjust the luminance in accordance with the brightness of the environment.

The first and second light emission patterns, such as light emission color, can freely be set according to the preference of the person being measured P who utilizes the external unit 30. The setting is made using, for example, the control unit 20. Since the external light source 51 includes a plurality of LEDs 511 along the outer peripheral edge of the circular circuit board 32 as shown in FIG. 6, the LEDs may emit light in sequence to draw a circle. Since, furthermore, the paired holder light sources 52 are provided on the right and left sides, respectively, the right-side holder light source 52 may emit light when the swallowing action is dominant on the right, and the left-side holder light source 52 may emit light when the swallowing action is dominant on the left.

The swallowing action measurement device 1 of the first embodiment configured as described above includes the holder 11 that is the measurement unit 10, which is attached to a neck region of the person being measured P when he or she eats his or her meal in order to measure the swallowing action of the person being measured P, to thereby detect sound associated with swallowing action (swallowing sound). When the detected swallowing sound is output from the sound detector as a measured sound signal, at least epiglottis closing sound, food bolus moving sound and epiglottis opening sound are extracted from the analysis unit 14 of the control unit 20. After that, the extracted epiglottis closing sound, food bolus moving sound and epiglottis opening sound are output from the analysis unit 14 as swallowing action information in association with the measured posture signal detected by the posture detector 13 based on the real time.

The determination unit 15 compares predetermined temporal characteristics and frequency characteristics, sound duration, etc., of each of the epiglottis closing sound, food bolus moving sound and epiglottis opening sound with predetermined temporal characteristics and frequency characteristics, sound duration, etc., of the standard sound signal stored in the memory 17. The determination unit 15 outputs a proper signal indicating that the swallowing action is determined to be proper while the deviation is within a predetermined range. The determination unit 15 also outputs an improper signal indicating that the swallowing action is determined to be improper when the deviation exceeds the predetermined range.

At this time, the measured sound signal detected by the swallowing action measurement device 1 varies from person being measured P to person being measured P. If, therefore, an average of swallowing sounds generated by the swallowing actions of a large number of persons is employed as a standard sound signal, the standard sound signal will always have a constant deviation even though it is a measured sound signal associated with the swallowing action most suitable for the person being measured P. It is thus desirable to calibrate the standard sound signal according to the person being measured P.

In the swallowing action measurement device 1 of the present embodiment, therefore, the standard sound signal is calibrated based upon the measured sound signal of the person being measured P, measured in the past. Specifically, the controller 16 averages the measured sound signals included in the unique swallowing information associated with the proper signal, among the past unique swallowing information stored in the memory 17, and replaces the averaged signal with the standard sound signal stored in the memory 17. This calibration may be performed each time the swallowing action measurement device 1 is attached to the person being measured P or it may be done based upon a plurality of items of past unique swallowing information each time the swallowing action measurement device 1 is attached and the measurement is actually made. Also, the past measured sound signals are not simply averaged, but a median obtained from the dispersion of the past measured sound signals may be employed as a standard sound signal.

The swallowing action measurement device 1 includes the posture detector 13. The unique swallowing information includes the measured posture signal along with the measured sound signal. The use of the measured posture signal further improves the reliability of the measurement results of the swallowing action measurement device 1. Specifically, the controller 16 averages the measured posture signals included in the unique swallowing information associated with the proper signal, among the past unique swallowing information stored in the memory 17, and stores the averaged signal in the memory 17 as a standard posture signal.

The standard posture signal is used to confirm whether the swallowing action measurement device 1 can be attached to the neck region of the person being measured P in the same position and at the same angle and whether the holder 11 of the measurement unit 10 is moved and shifted while the swallowing action measurement device 1 is used. Specifically, the determination unit 15 compares the measured posture signal with the standard posture signal, and output a proper signal while the deviation is within a predetermined range and outputs an improper signal when the deviation exceeds the predetermined range.

At this time, the determination unit 15 discriminates between an improper signal output to the measured sound signal and an improper signal output to the measured posture signal. The determination unit 15 also outputs a command signal other than the first and second command signals to be output from the controller 16 to correspond to the improper signal output to the measured posture signal. In the swallowing action support system 100, therefore, the notification unit 50 can output a notification capable of determining whether the swallowing action is improper and whether the insertion state of the swallowing action measurement device 1 is improper.

The swallowing action measurement device 1 of the present embodiment also includes a means for allowing intentional calibration in order to calibrate (set) a standard sound signal and a standard posture signal when the device is used for the first time. Specifically, the swallowing action measurement device 1 includes an input means for starting and terminating measurement for calibrating the sound detector 12 and the posture detector 13. The input means may be an operation button displayed on the display screen of the smartphone that is the control unit 20. In the swallowing action support system 100, the input means may be a touch sensor incorporated into the external unit 30, a touch sensor provided on the outer surface of the holder 11 that is the measuring unit 10 or the like.

The controller 16 is operated by the input means to store the measured sound signal and the measured posture signal, which are detected from the start to the end of the calibration, in the memory 17 as a standard sound signal and a standard posture signal, respectively. When the sound detector 12 and the posture detector 13 of the swallowing action measurement device 1 are calibrated, guidance to guide the operation procedures may be audio-output at the start of the calibration.

When the swallowing action measurement device 1 is used for the first time to perform calibration, it is also preferable to include a standard calibration liquid in advance as an appropriate amount of liquid (e.g., 3 to 5 ml) which is adjusted to an appropriate viscosity in order to make the swallowing action ideally.

In addition, the operation of calibrating the standard sound signal and the standard posture signal may be performed without fail each time the holder 11 of the measurement unit 10 is attached to the neck region of the person being measured P. In this case, a container containing the standard calibration liquid for a plurality of calibrations and a measurement instrument capable of measuring the standard calibration liquid for one calibration from the container may be included.

In the swallowing action measurement device 1 of the present embodiment configured as described above and the swallowing action support system 100 using this device, the first communication device 41 of the control unit 20 can be connected to the network 200 to which the database 201 and management terminal 202 are connected, as well as the second communication device 42 of the external unit 30, as shown in FIG. 1.

If, therefore, the controller 16 stores the unique swallowing information in the database 201 together with identification information of the person being measured P, the person being measured P need not have his or her own swallowing action measurement device 1 and can easily make the initial setting (calibration) of the swallowing action measurement device 1. When the swallowing action measurement device 1 includes an input means to be operated to perform the calibration of the sound detector 12 and the posture detector 13, if the input means is operated to input the identification information of the person being measured P, the controller 16 selects the unique swallowing information associated with the proper signal from the unique swallowing information stored in the database 201. After that, the controller 16 averages the measured sound signal and the measured posture signal included in the selected unique swallowing information and stores them in the memory 17 as a standard sound signal and a standard posture signal, respectively. When a standard sound signal and a standard posture signal associated in advance with the identification information of the person being measured P are prepared, they are read out of the database 201 and stored in the memory 17.

Furthermore, in a remote place, people can consult a specialist on their swallowing actions via the network 200 and use a server 203 capable of more advanced analysis than the analysis unit 14. They can also obtain the latest applications of the analysis unit 14, determination unit 15 and controller 16 via the network 200. The specialist can monitor the conditions of a plurality of persons being measured P on the management terminal 202.

For example, a function of determining that an improper swallowing action is likely to occur, based on signals detected by the sound detector 12 and the posture detector 13 before sound associated with a swallowing action is detected, to prevent the improper swallowing action from occurring, can be add to the swallowing action measurement device 1 in use.

Furthermore, the swallowing action measurement device 1 temporarily stores the measured sound signal detected by the sound detector 12 in the memory 17 when the measurement is started. When the determination unit 15 outputs the improper signal, the controller 16 stores the measured sound signal and the measured posture signal prior to the measured sound signal that was determined as epiglottis closing sound by the analysis unit 14 in the memory 17 as improper prediction information. Then, the determination unit 15 compares the predetermined temporal characteristics and frequency characteristics of the measured sound signal detected between the previous swallowing action and the subsequent swallowing action and the rate of change in the measured posture signal with the improper prediction information. When the deviation falls within a predetermined range, the determination unit 15 outputs a warning signal to predict the possibility of aspiration. When the controller 16 detects the warning signal, the notification unit 50 may make a notification to provide warning.

A swallowing action measurement device 1 and a swallowing action support system 100 according to a second embodiment of the present invention will be described with reference to FIGS. 7 to 9. In the following description, the configuration of the second embodiment having the same function as that of the swallowing action measurement device 1 and the swallowing action support system 100 of the first embodiment will be denoted by the same symbol as that in the first embodiment and their detailed descriptions will be referred to the corresponding description of the first embodiment.

Figure 7:
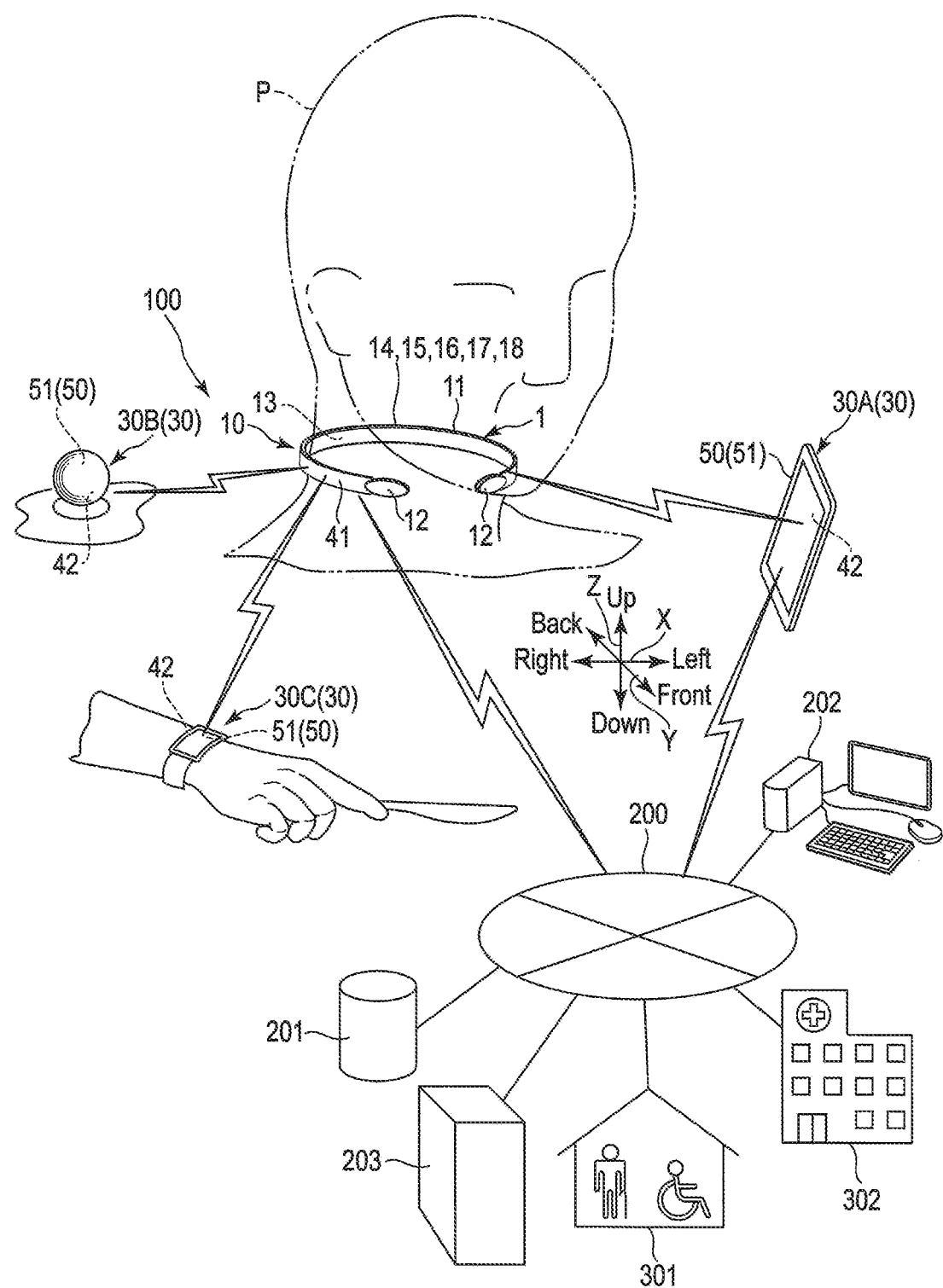
FIG. 7 is a perspective view showing a swallowing action support system including a swallowing action measurement device of a second embodiment of the present invention.

FIG. 7 is a perspective view showing a configuration of the swallowing action measurement device 1 of the second embodiment and the swallowing action support system 100 employing the swallowing action measurement device 1. FIG. 8 is a sectional view showing the swallowing action measurement device 1 of the second embodiment. FIG. 9 is a block diagram showing the minimum unit of the swallowing action support system 100 employing the swallowing action measurement device 1 of the second embodiment.

Figure 8:
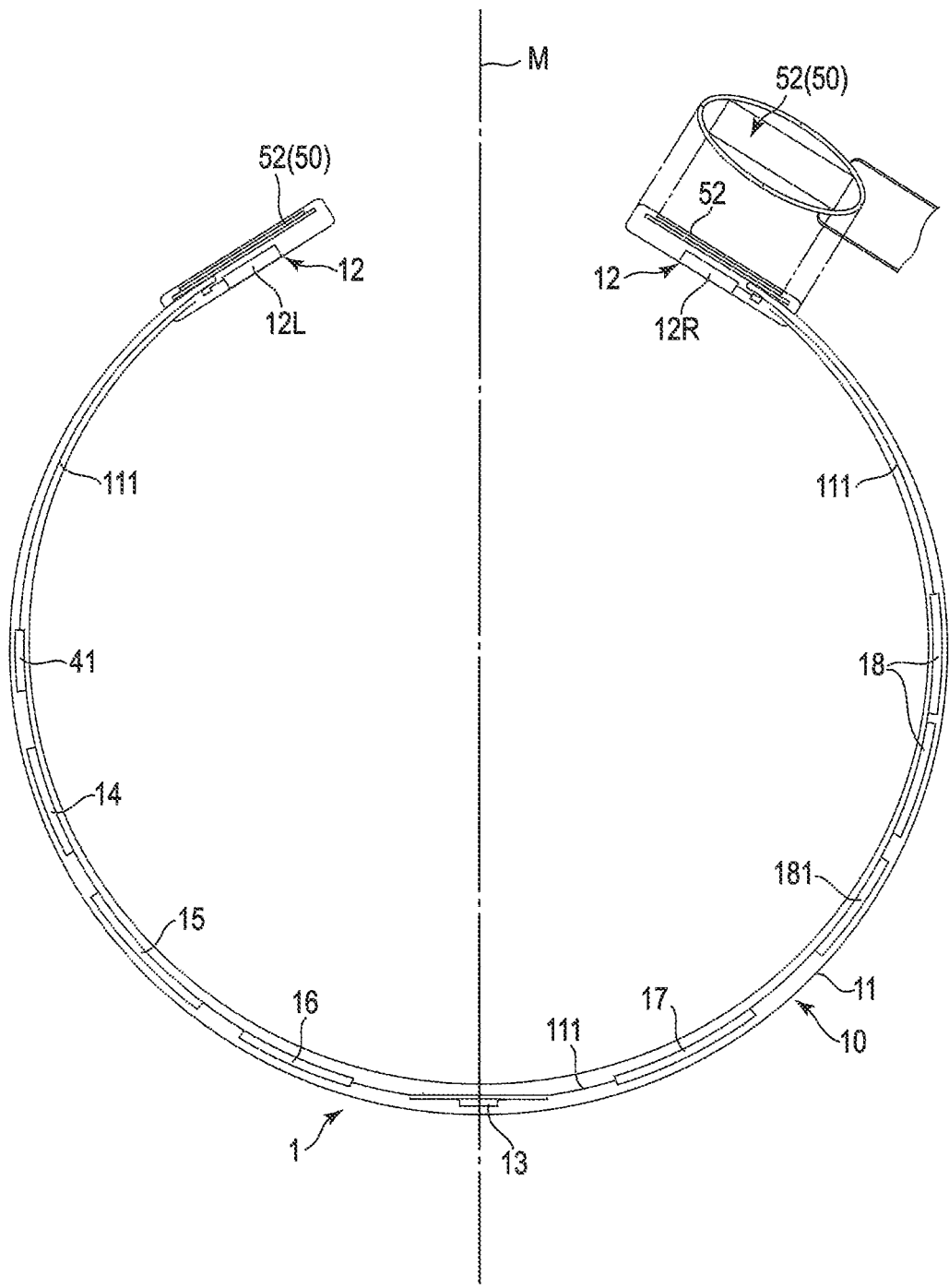
FIG. 8 is a sectional view of the swallowing action measurement device of FIG. 7.
Figure 9:
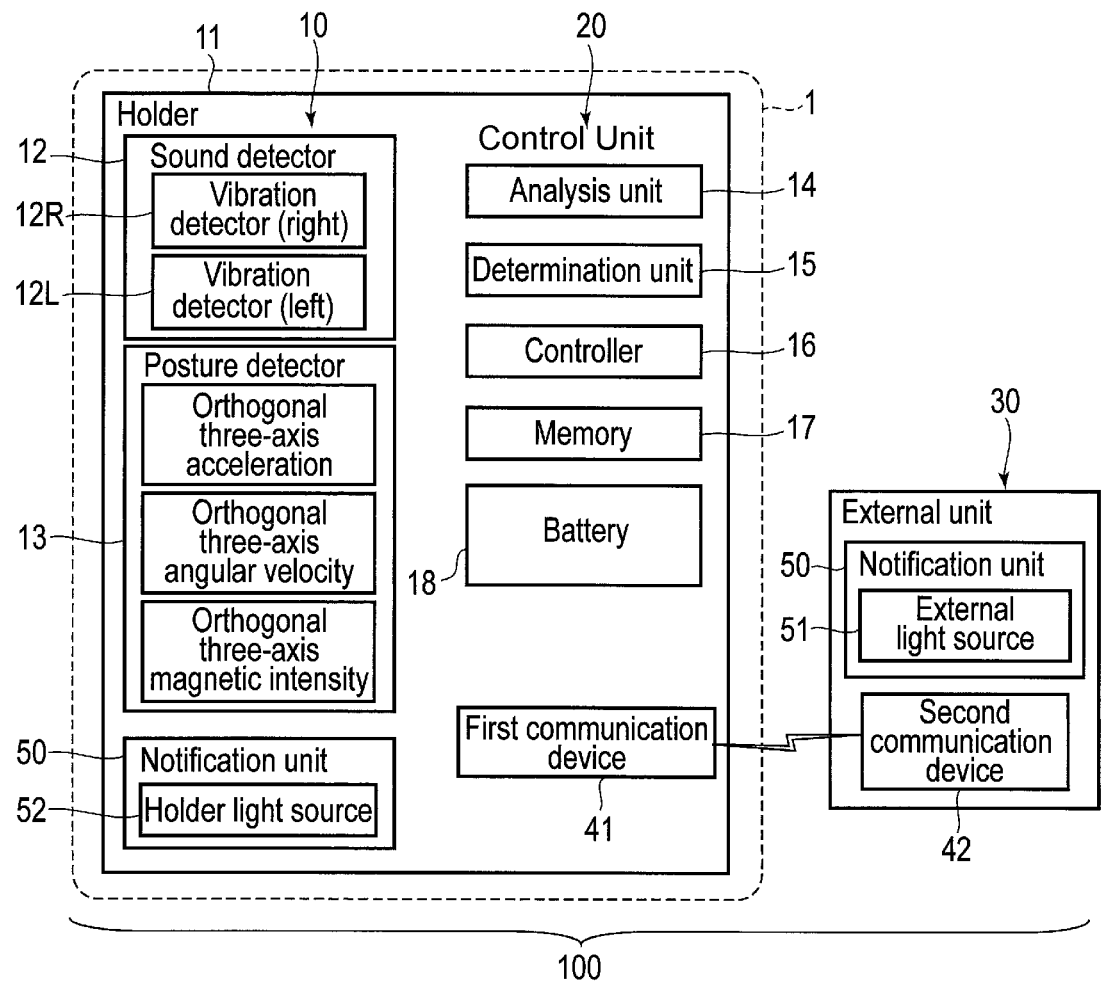
FIG. 9 is a block diagram of the swallowing action measurement device of FIG. 7.

The swallowing action measurement device 1 of the second embodiment includes a holder 11 having all the functions of a measurement unit 10 and a control unit 20, as shown in FIGS. 8 and 9. That is, the holder 11 incorporates a sound detector 12 and a posture detector 13 and also incorporates an analysis unit 14, a determination unit 15, a controller 16, a memory 17, a battery 18 and a first communication device 41. As in the first embodiment, the first communication device 41 can communicate with a second communication device 42 of an external unit 30 wirelessly and also communicate wirelessly with a network 200 to which a database 201 and a management terminal 202 are connected. The memory 17 may be provided with a connector through which a storage medium is inserted from the outside.

Thus, the swallowing action measurement device 1 of the present embodiment can be connected directly to the network 200 to store unique swallowing information in the database 201 together with the identification information of the person being measured P, browse the unique swallowing information stored in the database 201 from the management terminal 202, and use a server 203 capable of more advanced analysis than the analysis unit 14. In the first embodiment, a smartphone is used as the control unit 20 of the swallowing action measurement device 1, whereas in the present embodiment, not only a smartphone 30A can be used as one form of the external unit 30, but also it can be used as an operation device to browse the unique swallowing information stored in the memory 17 of the swallowing action measuring device 1 and read it therefrom. The smartphone 30A can also be used as an input means for changing the setting of the swallowing action measuring device 1.

Furthermore, the swallowing action measurement device 1 can be wirelessly connected to an external unit 30B similar to the external unit 30 of the first embodiment to configure the swallowing action support system 100. Also, the swallowing action measurement device 1 wirelessly communicates with a wristwatch-type mobile terminal, or what is called a smartwatch 30C and thus the smartwatch 30C can be used as the external unit 30 including an external light source 51 as a notification unit 50. When the swallowing action measurement device 1 is used as the swallowing action support system 100 away from home, no place for installing the external unit 30 is required, with the result that the opportunity to use the swallowing action measurement device 1 as the swallowing action support system 100 increases, and more unique swallowing information can be obtained.

In the swallowing action measurement device 1 of the second embodiment, the posture detector 13 and the first communication device 41 are built in the holder 11. If, therefore, the swallowing action measurement device 1 is introduced in a nursing home 301 such as a home for the elderly in which network 200 environment of wireless connection is improved and a hospital 302 as well, it can also be used to watch the active condition of the person being measured P.

Like the swallowing action measurement device 1 of the first embodiment, the swallowing action measurement device 1 includes a holder light source 52 in the holder as the notification unit 50 as shown in FIG. 8. The holder light source 52 is a display unit having a fixed area and can also display a simple figure and character. When the holder light source 52 is used as a display unit, it can display, for example, the charging state of the battery 18, the wireless communication state of the smartphone 30A, external unit 30B, smartwatch 30C and network 200.

The battery 18 may be charged via a connector. In the swallowing action measurement device 1 of the present embodiment, however, a power receiving coil 181 that generates power by electromagnetic induction is built in the holder 11, as shown in FIG. 8. The battery 18 can thus be charged by keeping the swallowing action measurement device 1 in an AC magnetic field generated by a dedicated device.

The swallowing action measurement device 1 may include a touch sensor on the outer surface of the holder 11, e.g., a portion of the outer surface on which the holder light source 52 is disposed, as an input means for calibrating the sound detector 12 and posture detector 13 as in the first embodiment. When the input means is operated, the controller 16 selects unique swallowing information associated with the proper signal from the unique swallowing information stored in the database 201 via the network 200 on the basis of the identification information of the person being measured P set in the swallowing action measurement device 1. Then, the controller 16 reads the measured sound signals and the measured posture signals included in the selected unique swallowing information, averages the signals, and stores the averaged signals in the memory 17 as a standard sound signal and a standard posture signal, respectively. The swallowing action measurement device 1 of the second embodiment is thus calibrated to conform to the person being measured P as soon as it is attached to the person being measured P. The input means may be operated to calibrate (set) the standard sound signal and the standard posture signal when the swallowing action measurement device 1 is used for the first time.

A swallowing action measurement device 1 and a swallowing action support system 100 according to a third embodiment of the present invention will be described with reference to FIGS. 10 to 12. The configuration of the third embodiment having the same function as that of the swallowing action measurement device 1 and the swallowing action support system 100 of each of the first and second embodiments will be denoted by the same symbol as that in each of the first and second embodiments and their detailed descriptions will be referred to the corresponding description of the first and second embodiments.

Figure 10:
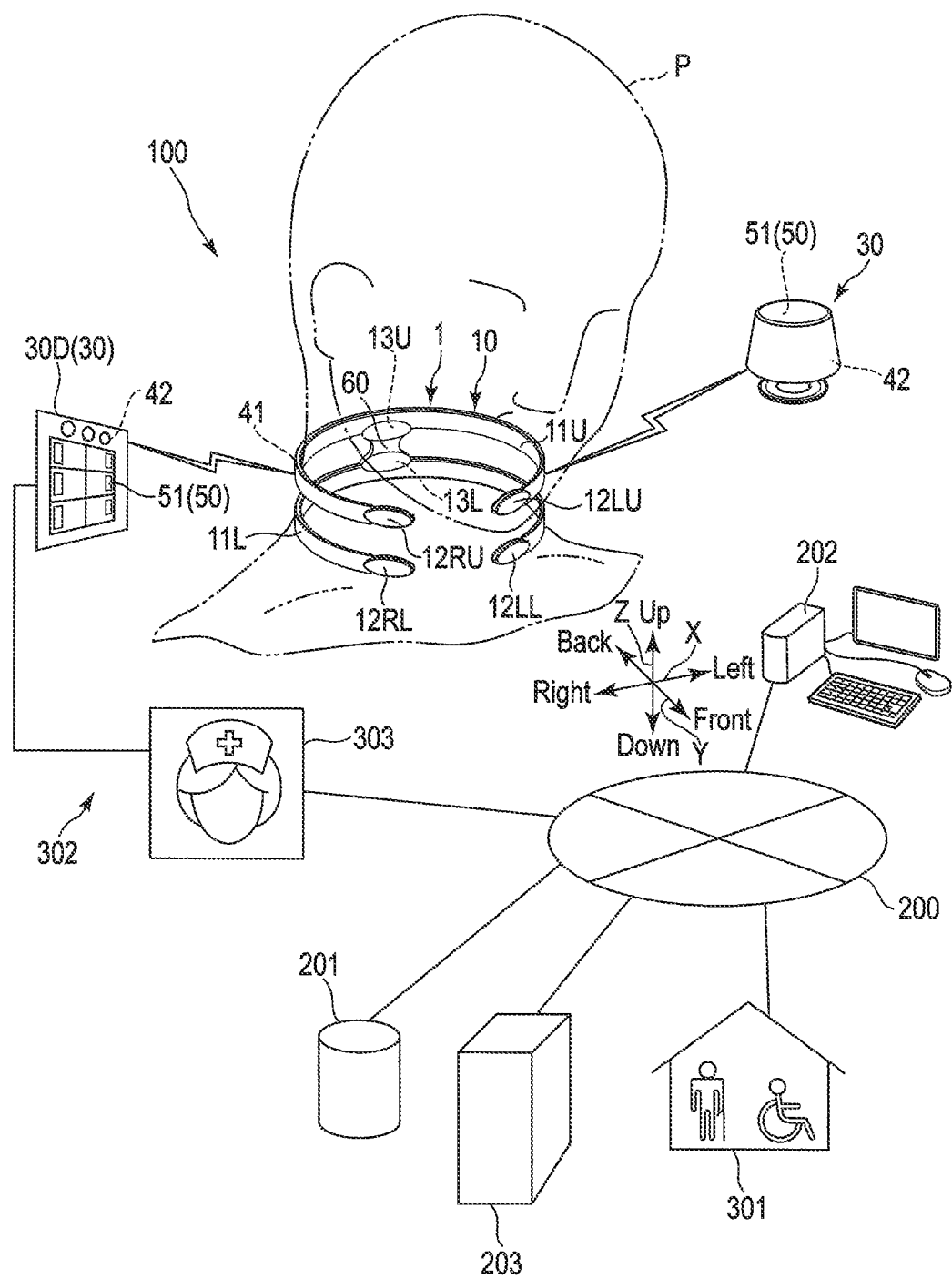
FIG. 10 is a perspective view showing a swallowing action support system including a swallowing action measurement device of a third embodiment of the present invention.

FIG. 10 is a perspective view showing a configuration of the swallowing action measurement device 1 of the third embodiment and the swallowing action support system 100 utilizing the swallowing action measurement device 1. The configuration of the swallowing action measurement device 1 of the third embodiment is that two swallowing action measurement devices 1 corresponding to the swallowing action measurement device 1 of the second embodiment are arranged vertically. The two swallowing action measurement devices 1 are coupled by a flexible joint 60 at a portion located in a rearward position when they are attached to the neck region. FIG. 11 is a perspective view of the swallowing action measurement device 1 of FIG. 10, viewed from upper right behind.

Figure 11:
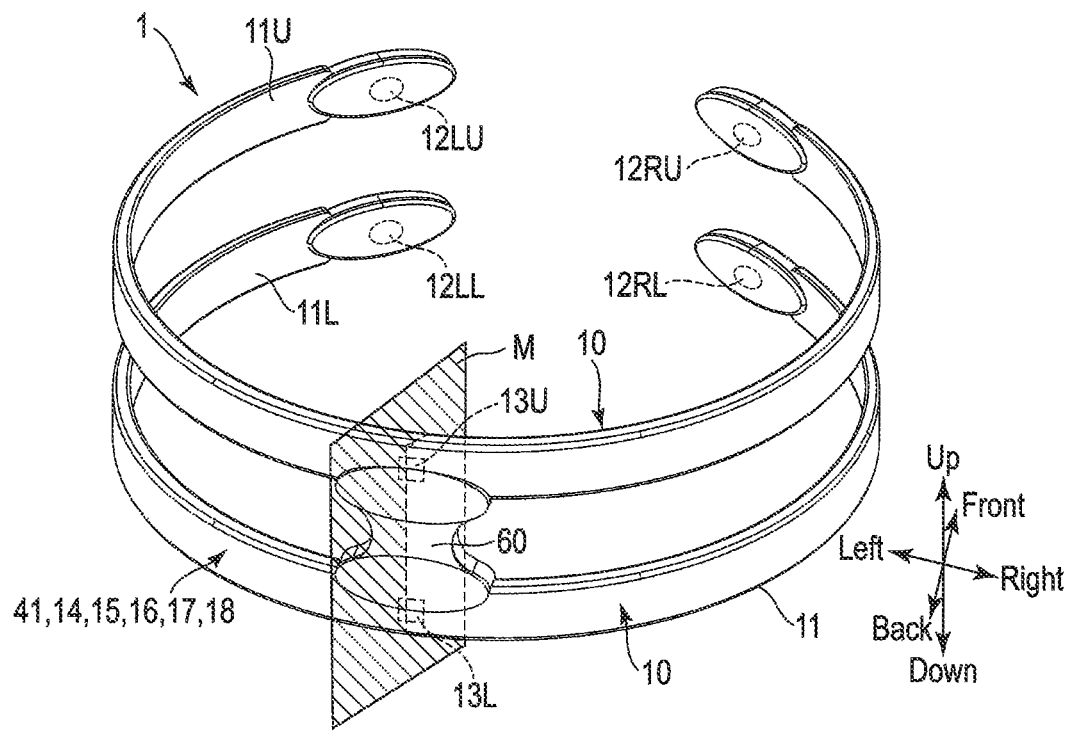
FIG. 11 is a perspective view of the swallowing action measurement device of FIG. 10, viewed from upper right behind.
Figure 12:
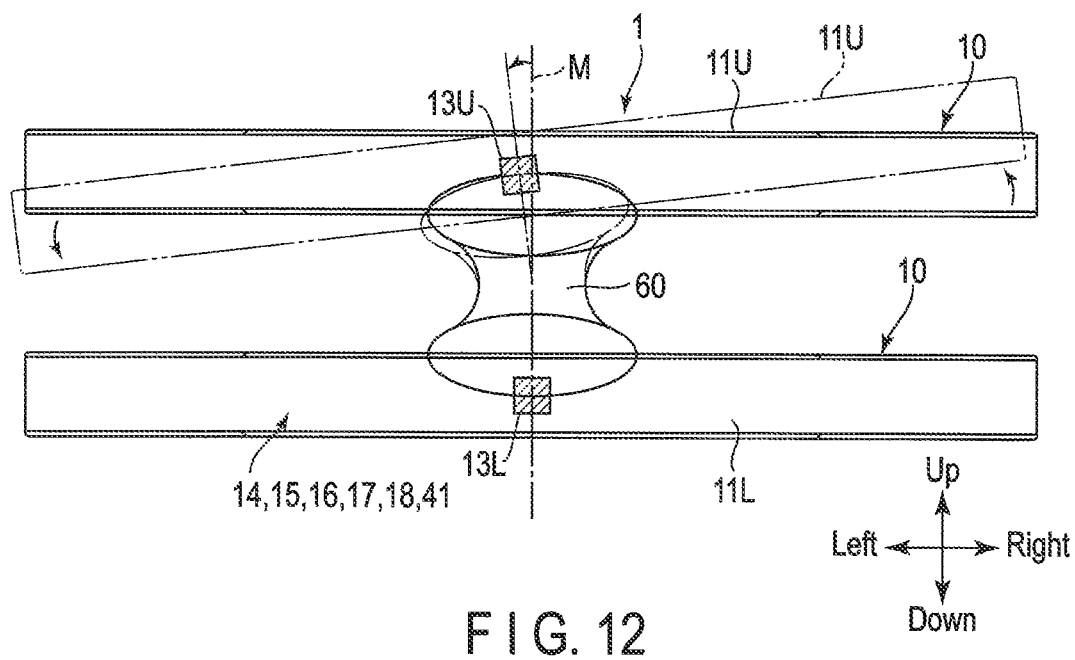
FIG. 12 is a rear side view of the swallowing action measurement device of FIG. 10.

As shown in FIG. 11, in the swallowing action measurement device 1 of the present embodiment, a sound detector 12 includes four vibration detectors 12RU, 12RL, 12LU and 12LL as a set of vibration detectors. The vibration detectors 12RU and 12LU are disposed plane-symmetrically with regard to the median plane M and so are the vibration detectors 12RL and 12LL. Also, the vibration detectors 12RU and 12RL are disposed along a direction in which a food bolus is moved by a swallowing action of a person being measured P and so are the vibration detectors 12LU and 12LL. The vibration detectors 12RU, 12RL, 12LU and 12LL each detect a measured sound signal and output it. A plurality of posture detectors 13 are disposed along a direction in which a food bolus is moved by a swallowing action. In the present embodiment, two posture detectors 13U and 13L are provided and each output a measured posture signal. Like in the first and second embodiments, the posture detectors 13U and 13L of the present embodiment each employ what is called a 9-axis sensor capable of sensing earth's magnetism, acceleration and angular velocity for orthogonal three axes.

In the swallowing action measurement device 1, the two posture detectors 13U and 13L are arranged vertically (along the Z axis) behind a holder located on the median plane M. If, therefore, for example, a relative rotation angle between an upper holder 11U and a lower holder 11L with the Z axis of the joint 60 centered is varied and a relative angle between the upper holder 11U and the lower holder 11L is varied by the joint 60 as shown in FIG. 12, a turn, a bending direction and a bending angle of the neck region can be detected accurately. FIG. 12 is a rear side view of the swallowing action measurement device 1. In FIG. 12, the solid line indicates that the upper holder 11U is parallel to the lower holder 11L, and a two-dot-one-dash virtual line indicates that the left side of the upper holder 11U is lowered. That is, the upper holder 11U indicated by the virtual line in FIG. 12 corresponds to a situation where the neck region of the person being measured P is tilted just to the left in FIG. 10.

Incidentally, the swallowing action measurement device 1 of the third embodiment may be configured to couple two swallowing action measurement devices, which are identical with the swallowing action measurement device 1 of the second embodiment, vertically by a joint 60, that is, to include two analysis units 14, two determination units 15, two controllers 16 and two memories 17 as well as two sound detectors 12 and two posture detectors 13. Alternatively, the swallowing action measurement device 1 of the third embodiment may have only one configuration other than each of the sound detector 12 and the posture detector 13.

As described above, in the swallowing action measurement device 1 configured to include the sound detector 12 and the posture detector 13, the analysis unit 14 can calculate the speed of motion of a food bolus based on a real-time difference between predetermined temporal characteristics and frequency characteristics of the measured sound signal detected by a pair of vibration detectors 12RU and 12RL and those of the measured sound signal detected by a pair of vibration detectors 12LU and 12LL. The calculated motion speed is added to the swallowing action information and output. The analysis unit 14 can also calculate a turn, a bending direction and a bending angle of the neck region based upon the measured posture signals output from the posture detectors 13U and 13L. The calculated turn, bending direction and bending angle of the neck region are added to the swallowing action information and output.

Information of the motion speed is useful in determining whether it is easy for the person being measured P to swallow food. If, furthermore, information of the turn, bending direction and bending angle is evaluated together with proper and improper signals output from the determination unit 15, the information is useful in determining the swallowing ability or dysphagia of the person being measuring P.

If the swallowing action measurement device 1 of the third embodiment configured as described above is attached to the person being measured P who has to take a meal with his or her neck region bent, as shown in FIG. 10, a proper swallowing action can easily be reproduced. In particular, even though the same helper cannot help the person being measured P who cannot eat a meal by himself or herself but always needs a helper, the optimum bending angle, bending direction and turn of the neck region to allow a proper swallowing action can be reproduced accurately by the swallowing action measurement device 1.

Furthermore, according to the swallowing action support system 100 employing the swallowing action measurement device 1, the first communication device 41 carries out wireless communication with the external unit 30 to notify whether the swallowing action is proper or improper. Therefore, even though the holder light source 52 that is the notification unit 50 of the swallowing action measurement device 1 is hidden by an apron, a towel or the like during the meal, if the state of the external unit 30 is observed, both the helper and the person being measured P can know whether the swallowing action is proper or improper at the same time, that is, they can share the information.

Furthermore, in the nursing home 301 such as a home for the elderly and the hospital 302, the first communication device 41 of the swallowing action measurement device 1 may be provided as the external unit 30 to allow wireless communication with, for example, a corridor light 30D of each room. In the case of the hospital 302, the corridor light 30D is directly connected to a nurse station 303 in which nurses are standing by. If, therefore, the swallowing action measurement device 1 notifies the nurse station 303 through the corridor light 30D that the swallowing action of, for example, a person being measured P who becomes bedridden is improper, the nurses can quickly respond to the improper swallowing action.

Incidentally, since the swallowing action measurement device 1 of each of the first to third embodiments includes the posture detector 13, even though it is attached to the neck region upside down, it need not be attached again by recognizing the vertical and horizontal directions again immediately based upon a signal obtained from the posture detector 13. Also, the external unit 30 may be a head-mounted display.

The swallowing action measurement device 1 and the swallowing action support system 100 according to the first to third embodiments have been described. These embodiments have been presented by way of example only for easy understanding to reduce the present invention to practice, and are not intended to limit the scope of the invention to the embodiments. The present invention can be reduced to practice by replacing each element with another element having the same function without departing from the spirit of the invention, and the element is also included in the present invention. The present invention can also be reduced to practice by combining some of the elements described in the embodiments or replacing them.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A swallowing action measurement device comprising:
   a holder configured to be fitted to a neck region of a person being measured from behind;
   a sound detector mounted in the holder and configured to be in contact with an outer side surface of the neck region close to an epiglottis and configured to detect sound associated with at least a swallowing action of the person being measured and output a measured sound signal;
   a posture detector system configured to detect a posture of the person being measured and output a measured posture signal; and
   a computing device including an analysis unit configured to discriminate among epiglottis closing sound, food bolus moving sound and epiglottis opening sound from the measured sound signal based upon frequency characteristics and output the epiglottis closing sound, food bolus moving sound and epiglottis opening sound as a series of items of swallowing action information in association with the measured posture signal in real time when each sound is detected,
   the computing device including a determination unit configured to compare predetermined temporal characteristics and frequency characteristics of the measured sound signal included in the swallowing action information in real time with predetermined temporal characteristics and frequency characteristics of a standard sound signal preset for the swallowing action, and output a proper signal indicating that the swallowing action is in a proper state while a deviation is within a predetermined range and output an improper signal indicating that the swallowing action is in an improper state when the deviation exceeds the predetermined range;

the computing device including a controller configured to output the swallowing action information as swallowing information unique to the person being measured in association with the proper signal and the improper signal; and the computing device including a memory configured to store the standard sound signal and the swallowing information, wherein:

the sound detector includes a single vibration detector or a pair of vibration detectors configured to be disposed along a direction in which a food bolus is moved by the swallowing action;

the analysis unit is configured to calculate a speed of motion of the food bolus based on the measured sound signal detected by the single vibration detector or the pair of vibration detectors and outputs the speed of motion in addition to the swallowing action information;

the controller averages the measured sound signals included in the swallowing information associated with the proper signal, among past unique swallowing information stored in the memory, and replaces the standard sound signal stored in the memory with an averaged signal; and the predetermined temporal characteristics include a sound duration.

2. The device of claim 1, wherein:

the sound detector includes the single vibration detector or pair of vibration detectors configured to be disposed plane-symmetrically with regard to a median plane of the person being measured; and the analysis unit is configured to determine whether the swallowing action is dominant on right or dominant on left, based on a difference between right and left measured sound signals detected by the pair of vibration detectors, and the analysis unit is configured to output a determination result in addition to the swallowing action information.

3. The device of claim 1, wherein:

the sound detector includes the single vibration detector or pair of vibration detectors configured to be disposed plane-symmetrically with regard to a median plane of the person being measured; and the analysis unit is configured to determine whether the swallowing action is dominant on right or dominant on left based on a difference between right and left measured sound signals detected by the single vibration detector or pair of vibration detectors and the measured posture signal, and the analysis unit is configured to output a determination result in addition to the swallowing action information.

4. The device of claim 1, wherein:

the computing device further comprises a control unit located away from the holder and within a range where the control unit is allowed to be operated by the person being measured and equipped with the analysis unit, the determination unit, the controller and the memory;

a first communication circuit built in the holder and configured to transmit a signal including at least the measured sound signal and the measured posture signal; and a second communication circuit built in the control unit and configured to receive a signal including at least the measured sound signal and the measured posture signal.

5. The device of claim 4, wherein the first communication circuit and the second communication circuit wirelessly communicate with each other.

6. The device of claim 1, wherein the analysis unit, the determination unit, the controller and the memory are incorporated into the holder.

7. The device of claim 6, further comprising a battery mounted on the holder and configured to supply power to the sound detector, the posture detector system, the analysis unit, the determination unit, the controller and the memory.

8. The device of claim 1, further comprising input elements for starting and terminating measurement for calibration of the sound detector and the posture detector system, wherein the controller is configured to store the measured sound signal and the measured posture signal, which are detected from start to end of the calibration, in the memory as the standard sound signal and a standard posture signal, respectively.

9. The device of claim 8, wherein the determination unit is configured to compare the measured posture signal with the standard posture signal, and the determination unit is configured to output the proper signal while a deviation is within a predetermined range and outputs the improper signal when the deviation exceeds the predetermined range.

10. The device of one of claims 8 and 9, wherein the controller is configured to average the measured posture signals included in the swallowing information associated with the proper signal, among past unique swallowing information stored in the memory, and the controller is configured to store an averaged signal in the memory as the standard posture signal.

11. A swallowing action measurement device comprising:

a holder configured to be fitted to a neck region of a person being measured from behind;

a sound detector mounted in the holder and configured to be in contact with an outer side surface of the neck region close to an epiglottis and configured to detect sound associated with at least a swallowing action of the person being measured and output a measured sound signal;

a posture detector system configured to detect a posture of the person being measured and output a measured posture signal; and a computing device including an analysis unit configured to discriminate among epiglottis closing sound, food bolus moving sound and epiglottis opening sound from the measured sound signal based upon frequency characteristics and output the epiglottis closing sound, food bolus moving sound and epiglottis opening sound as a series of items of swallowing action information in association with the measured posture signal in real time when each sound is detected, the computing device including a determination unit configured to compare predetermined temporal characteristics and frequency characteristics of the measured sound signal included in the swallowing action information in real time with predetermined temporal characteristics and frequency characteristics of a standard sound signal preset for the swallowing action, and output a proper signal indicating that the swallowing action is in a proper state while a deviation is within a predetermined range and output an improper signal indicating that the swallowing action is in an improper state when the deviation exceeds the predetermined range;

the computing device including a controller configured to output the swallowing action information as swallowing information unique to the person being measured in association with the proper signal and the improper signal; and the computing device including a memory configured to store the standard sound signal and the swallowing information, wherein:

the posture detector system includes a plurality of posture detectors configured to be disposed along a direction in which a food bolus is moved by the swallowing action and each configured to output the measured posture signal; and the analysis unit is configured to calculate a turn, a bending direction and a bending angle of the neck region based on the measured posture signal output from each of the plurality of posture detectors and outputs the turn, bending direction and bending angle in addition to the swallowing action information.

12. The device of one of claims 1 and 11, wherein the posture detector system is attached to the holder, the holder is configured to be located on a median plane of the person being measured, wherein the posture detector system includes an electronic compass configured to detect magnetic intensity of earth's magnetism for three orthogonal axes, and configured to output a measured posture signal including the magnetic intensity.

13. The device of claim 12, wherein the posture detector system is configured to detect acceleration in a direction along the three orthogonal axes and angular velocity with each of the three orthogonal axes as a center axis and outputs the acceleration and the angular velocity with the acceleration and the angular velocity included in the measured posture signal.

14. The device of claim 12, wherein the sound detector includes a pair of vibration detectors configured to be disposed plane-symmetrically with regard to the median plane.

15. The device of claim 11, wherein:

the controller averages the measured sound signals included in the swallowing information associated with the proper signal, among past unique swallowing information stored in the memory, and replaces the standard sound signal stored in the memory with an averaged signal, and the predetermined temporal characteristics include a parameter that varies with a fluidity of a food bolus.

16. A swallowing action support system comprising:

a holder configured to be fitted to a neck region of a person being measured from behind, wherein the holder is configured to be located on a median plane of the person being measured;

a sound detector mounted in the holder and configured to be in contact with an outer side surface of the neck region close to an epiglottis and configured to detect sound associated with at least a swallowing action of the person being measured and output a measured sound signal;

a posture detector system attached to the holder, the holder configured to be located on a median plane of the person being measured, the posture detector system including an electronic compass to detect magnetic intensity of earth's magnetism for three orthogonal axes, and configured to output a measured posture signal including the magnetic intensity;

a computing device including an analysis unit configured to discriminate among epiglottis closing sound, food bolus moving sound and epiglottis opening sound from the measured sound signal based upon frequency characteristics and output the epiglottis closing sound, food bolus moving sound and epiglottis opening sound as a series of items of swallowing action information in association with the measured posture signal in real time when each sound is detected;

the computing device including a determination unit configured to compare predetermined temporal characteristics and frequency characteristics of the measured sound signal included in the swallowing action information in real time with predetermined temporal characteristics and frequency characteristics of a standard sound signal preset for the swallowing action, and the determination unit is configured to output a proper signal indicating that the swallowing action is in a proper state while a deviation is within a predetermined range and output an improper signal indicating that the swallowing action is in an improper state when the deviation exceeds the predetermined range;

the computing device including a controller configured to output the swallowing action information as swallowing information unique to the person being measured in association with the proper signal and the improper signal and output a first command signal corresponding to the proper signal and a second command signal corresponding to the improper signal;

a notification circuit including a notification unit configured to make a first notification in response to the first command signal and make a second notification different from the first notification, in response to the second command signal; and the computing device including a memory configured to store the standard sound signal and unique swallowing information, wherein:

the sound detector includes a pair of vibration detectors configured to be disposed along a direction in which a food bolus is moved by the swallowing action;

the posture detector system includes a plurality of posture detectors configured to be disposed along a direction in which a food bolus is moved by the swallowing action and each configured to output the measured posture signal;

the analysis unit is configured to calculate a speed of motion of the food bolus based on the measured sound signal detected by the pair of vibration detectors and outputs the speed of motion in addition to the swallowing action information, and calculates a turn, a bending direction and a bending angle of the neck region based on the measured posture signal output from each of the plurality of posture detectors and outputs the turn, bending direction and bending angle in addition to the swallowing action information;

the controller averages the measured sound signals included in the swallowing information associated with the proper signal, among past unique swallowing information stored in the memory, and replaces the standard sound signal stored in the memory with an averaged signal, the predetermined temporal characteristics include a sound duration.

17. The system of claim 16, wherein the posture detector system is configured to detect acceleration in a direction along the three orthogonal axes and angular velocity with each of the three orthogonal axes as a center axis and outputs the acceleration and the angular velocity with the acceleration and the angular velocity included in the measured posture signal.

18. The system of one of claims 16 and 17, further comprising:
an external unit located away from the holder and within a range where the external unit is allowed to be perceived by the person being measured;
a first communication circuit configured to transmit the first command signal and the second command signal wirelessly; and
a second communication circuit built in the external unit and configured to receive the first command signal and the second command signal wirelessly,
wherein the notification unit includes an external light source disposed in at least the external unit and is configured to cause the external light source to emit light in a first light emission pattern as the first notification when the notification unit detects the first command signal and cause the external light source to emit light in a second light emission pattern other than the first light emission pattern, as the second notification when the notification unit detects the second command signal.

19. The system of claim 18, comprising a control unit located away from the holder and within a range where the control unit is allowed to be operated by the person being measured and equipped with the analysis unit, the determination unit, the controller, the memory and the first communication circuit.

20. The system of claim 18, wherein the holder is equipped with the analysis unit, the determination unit, the controller, the memory and the first communication circuit.

21. The system of claim 18, wherein:
the first communication circuit is connectable to a network to which a database and a management terminal are connected; and
the controller is configured to store the swallowing information in the database together with identification information of the person being measured.

22. The system of claim 21, further comprising input elements operated for calibration of the sound detector and the posture detector,
wherein when the input elements are operated, the controller averages the measured sound signals and the measured posture signals included in the unique swallowing information associated with the proper signal based on the identification information and stores averaged signals in the memory as the standard sound signal and a standard posture signal, respectively.

23. The system of claim 16, wherein the notification unit includes a pair of holder light sources disposed in the holder configured to be plane plane-symmetric with regard to the median plane and the notification unit is configured to cause the holder light sources to emit light in a first light emission pattern as the first notification when the notification unit detects the first command signal and cause the holder light sources to emit light in a second light emission pattern other than the first light emission pattern, as the second notification when the notification unit detects the second command signal.

* * * * *